United States Patent [19]

Kawada

[11] Patent Number: 5,885,606
[45] Date of Patent: Mar. 23, 1999

[54] POISON BAIT FOR CONTROLLING PEST INSECTS

[75] Inventor: Hitoshi Kawada, Osaka-fu, Japan

[73] Assignee: Sumitomo Chemical Company, Limited, Osaka, Japan

[21] Appl. No.: 572,007

[22] Filed: Dec. 14, 1995

[51] Int. Cl.[6] .................................................. A61N 25/08
[52] U.S. Cl. ........................................... 424/410; 424/405
[58] Field of Search ..................................... 424/410, 405; 514/490

[56] References Cited

U.S. PATENT DOCUMENTS 4,834,977  5/1989  Kohama et al. ........................ 424/405
4,891,385  1/1990  Synek ...................................... 514/490

FOREIGN PATENT DOCUMENTS 92407565  10/1992  Australia .

*Primary Examiner*—Thurman K. Page
*Assistant Examiner*—D. Faulkner
*Attorney, Agent, or Firm*—Sughrue, Mion, Zinn, Macpeak & Seas, PLLC

[57] ABSTRACT

The present invention relates to a poison bait for controlling pest insects comprising (a) an insecticidally active ingredient, (b) a sauce for seasoning or a sauce spice flavor, (c) a vegetable oil and, if necessary, (d) at least one of grain powder, dextrin and sugar. The inventive poison bait controls pest insects such as cockroaches and the like based on feeding preference.

15 Claims, No Drawings

POISON BAIT FOR CONTROLLING PEST INSECTS

FIELD OF THE INVENTION

The present invention relates to a poison bait for controlling pest insects, suitable for use in controlling pest insects, particularly in controlling cockroaches.

BACKGROUND OF THE INVENTION

Controlling of pest insects, such as cockroaches, by feeding poison bait containing an insecticidally active ingredient, has been routinely conducted. However, since the feeding preference of pest insects to poison bait has not been always good, the efficacy in controlling pest insects using poison bait has still not been satisfactory.

SUMMARY OF THE INVENTION

The present invention provides a poison bait for controlling pest insects which is excellent in feeding preference of pest insects, particularly cockroaches.

More precisely, the present invention provides a poison bait for controlling pest insects comprising (a) an insecticidally active ingredient, (b) a sauce for seasoning or a sauce spice flavor and (c) a vegetable oil.

Although the poison bait according to the present invention is excellent as such in the feeding preference of pest insects, particularly of cockroaches, it is preferred to add (d) at least one kind selected from the group consisting of grain powder, dextrin and sugar, in order to enhance the feeding preference.

DETAILED DESCRIPTION OF THE INVENTION

The insecticidally active ingredient used in the present invention may be not only substances having insecticidal activities such as pyrethroid compounds, organophosphorus compounds, carbamate compounds, N-aryldiazole compounds, hydrazone compounds, sulfonamide compounds, natural pesticidal compounds, boric acid and the like but also insect growth regulators such as juvenile hormone analogues, chitin-synthesis inhibitors and the like as well as a mixture of at least two kinds thereof.

Specific examples of said insecticidally active ingredients are shown below. It is to be appreciated that any isomer having said activity or mixtures of such isomers may be used.

(1) 5-benzyl-3-furylmethyl chrysanthemate,
(2) 3,4,5,6-tetrahydrophthalimidomethyl chrysanthemate,
(3) 3-phenoxybenzyl chrysanthemate,
(4) 3-phenoxybenzyl 3-(2,2-dichlorovinyl)-2,2-dimethylcyclopropanecarboxylate,
(5) 2-methyl-4-oxo-3-(2-propenyl)cyclopent-2-enyl chrysanthemate,
(6) 1-ethynyl-2-methyl-2-pentenyl chrysanthemate,
(7) 2-methyl-4-oxo-3-(2-propinyl)cyclopent-2-enyl chrysanthemate,
(8) α-cyano-3-phenoxybenzyl chrysanthemate,
(9) 2-methyl-4-oxo-3-(2-propenyl)cyclopent-2-enyl 2,2,3,3-tetramethylcyclopropanecarboxylate,
(10) 2,3,5,6-tetrafluoro-4-methylbenzyl 3-(2,2-dichorovinyl)2,2-dimethylcyclopropanecarboxylate,
(11) 2,3,5,6-tetrafluorobenzyl 3-(2,2-dichlorovinyl)-2,2-dimethylcyclopropanecarboxylate,
(12) α-cyano-3-phenoxybenzyl 2,2-dimethyl-3-(1,2,2,2-tetrabromoethyl)cyclopropanecarboxylate,
(13) α-cyano-3-phenoxybenzyl 2-(4-chlorophenyl)-3-methylbutyrate,
(14) α-cyano-3-phenoxybenzyl 2,2,3,3-tetramethylcyclopropanecarboxylate,
(15) α-cyano-3-phenoxybenzyl 3-(2,2-dichlorovinyl)-2,2-dimethylcyclopropanecarboxylate,
(16) α-cyano-3-phenoxybenzyl 2-(2-chloro-4-trifluoromethylanilino)-3-methylbutyrate,
(17) 2-(4-ethoxyphenyl)-2-methylpropyl 3-phenoxybenzyl ether,
(18) O,O-dimethyl 0-(3-methyl-4-nitrophenyl) phosphorothioate,
(19) 2,2-dichlorovinyl dimethyl phosphate,
(20) O,O-diethyl 0-(2-isopropyl-6-methyl-4-pyrimidinyl) phosphorothioate,
(21) (E)-O-2-isopropoxycarbonyl-1-methylvinyl O-methyl ethylphosphorothioate,
(22) O,O-diethyl O-(3,5,6-trichloro-2-pyridinyl) phosphorothioate,
(23) O,O-dimethyl O-(3,5,6-trichloro-2-pyridinyl) phosphorothioate,
(24) S-6-chloro-2,3-dihydro-2-oxo-1,3-oxazolo[4,5-b]pyridin-3-yl-methyl O,O-dimethyl phosphorothioate,
(25) 5-methoxy-3-(2-methoxyphenyl)-1,3,4-oxadiazol-2 (3H)-one,
(26) 2-(1-methylethoxy)phenyl methylcarbamate,
(27) 1-naphthyl methylcarbamate,
(28) 4-(2-bromo-1,1,2,2-tetrafluoroethyl)-1-(3-chloro-5-trifluoromethylpyridin-2-yl)-2-methylimidazole,
(29) 5-amino-3-cyano-1-(2,6-dichloro-4-trifluoromethylphenyl)-4-trifluoromethylsulfinylpyrazole,
(30) 5-amino-3-cyano-1-(2,6-dichloro-4-trifluoromethylphenyl)-4-trifluoromethylthiopyrazole,
(31) tetrahydro-5,5-dimethyl-2(1H)-pyrimidinone [3-[4-(trifluoromethyl)phenyl]-1-[2-[4-(trifluoromethyl)phenyl]-ethenyl]-2-propenylidene]hydrazone,
(32) N-ethyl perfluorooctanesulfonamide,
(33) Abamectin,
(34) boric acid,
(35) 2-[1-methyl-2-(4-phenoxyphenoxy)ethoxy]pyridine,
(36) isopropyl 11-methoxy-3,7,11-trimethyldodeca-2,4-dienoate,
(37) ethyl 3,7,11-trimethyldodeca-2,4-dienoate,
(38) 1-(4-chlorophenyl)-3-(2,6-difluorobenzoyl)urea,
(39) 1-(3,5-dichloro-2,4-difluorophenyl)-3-(2,6-difluorobenzoyl)urea,
(40) 1-(4-trifluoromethoxyphenyl)-3-(2-fluorobenzoyl)urea,
(41) N-cyclopropyl-1,3,5-triazine-2,4,6-triamine,
(42) 2-t-butylimino-3-isopropyl-5-phenylperhydro-1,3,5-thiadiazin-4-one The amount of the insecticidally active ingredient to be contained in the poison bait for controlling pest insects according to the present invention may vary depending upon the kind of the insecticidally active ingredient and generally 0.05–10% by weight. The effect of controlling pest insects of the poison bait can be increased by adding a synergist such as α-[2-(2-butoxyethoxy)ethoxy]-4,5-methylenedioxy-2-propyltoluene, octachlorodipropyl ether, isobornyl thiocyanatoacetate, N-(2-ethylhexyl)bicyclo[2.2.1]hept-5-ene-2,3-dicarboximide, and the like.

The sauce for seasoning used in the present invention includes Worcester sauce, medium thick sauce, thick sauce, prescribed in Japanese Agricultural Standard, and the like, among which Worcester sauce is the most preferred. The sauce for seasoning used in the present invention can be prepared by the method, for example, described in p.222–4 of "Koryo no Jiten" published by Asakura Publishing Co., Ltd. These sauces for seasoning may be used as such or used in the form of sauce powder prepared by pulverization of the sauces for seasoning, for example, by lyophilization, or by addition of a carbohydrate such as starch.

The sauce for seasoning may usually be incorporated in the poison bait for controlling pest insects of the present invention in an amount of 1–20% by weight.

Instead of the sauce for seasoning, a sauce spice flavor may also be used. As the sauce spice flavor may be a spice oil mixture as seen in , for example, p.289 of "Koryo no Jiten" published by Asakura Publishing Co., Ltd. Examples of the sauce spice flavors are sauce flavor No.B-82404 or saucemicron No.600 (both made by Takasago International Corporation).

The sauce spice flavor may usually be incorporated in the poison bait for controlling pest insects of the present invention in an amount of 0.01–2% by weight.

The vegetable oil used in the present invention includes, for example, vegetable cooking oils such as soybean oil, sesame oil, rape seed oil, wheat germ oil, cotton seed oil, corn oil, sunflower oil, coconut oil and the like, among which soybean oil, sesame oil, rape seed oil and a mixture of at least two kind of them are preferred. The vegetable oil is usually incorporated in the poison bait for controlling pest insects according to the present invention in an amount of 10–50% by weight.

It is preferred that the poison bait for controlling pest insects according to the present invention further comprises grain powder, dextrin, sugar or at least two kinds thereof. The grain powder includes, for example, starch such as that of corn, potato, sweet potato and the like, wheat flour, rice flour, corn flour, potato flour and the like. The dextrin includes, for example, those obtained by hydrolyzing starch of corn, potato, sweet potato, wheat, rice and the like with acid, heat or amylase or the like. The sugar includes, for example, sucrose, glucose, granulated sugar, fructose, lactose, raw sugar, brown sugar, soft sugar and the like. The grain powder, dextrin, sugar or at least two kinds thereof may be incorporated in the poison bait for controlling pest insects according to the present invention in an amount in total of 40–85% by weight.

Further, the poison bait for controlling pest insects according to the present invention may include, if necessary, antioxidant, preservative, agent for preventing from eating by mistake, diluent, flavor and the like.

The antioxidant which can be used includes, for example, erythorbic acid, sodium erythorbate, dibutylhydroxytoluene, $\alpha$-tocopherol, nordihydroguaiaretic acid, methylhydroxyanisol, propyl gallate, guaiac resin, L-cysteine hydrochloride and the like. The preservative includes, for example, benzoic acid, sodium benzoate, salicylic acid, sorbic acid, potassium sorbate, dehydroacetic acid, sodium dehydroacetate, isobutyl p-hydroxybenzoate, isopropyl p-hydroxybenzoate, ethyl p-hydroxybenzoate, butyl p-hydroxybenzoate, propyl p-hydroxybenzoate, calcium propionate, sodium propionate and the like. The agent for preventing from eating by mistake includes, for example, cayenne pepper, Amaranth, Amaranth aluminum lake, Erythrosine, Erythrosine aluminum lake, New coccine, Phloxine, Rose Bengal, Acid Red, tartrazine, tartrazine aluminum lake, Sunset Yellow FCF, Sunset Yellow FCF aluminum lake, Fast Green FCF, Fast Green FCF aluminum lake, Brilliant Blue FCF, Brilliant Blue FCF aluminum lake, indigo carmine, indigo carmine aluminum lake, $\beta$-carotene, copper chlorophyll, and the like. The diluent includes, for example, white carbon, diatomaceous earth, crystalline cellulose, kaolin, talc, bentonite, zeolite, sepiolite, attapulgite and the like. The flavor includes, for example, cheese flavor, butter flavor, peanut flavor, strawberry flavor, milk flavor and the like.

The poison bait for controlling pest insects according to the present invention may also contain a known attractant.

The poison bait for controlling pest insects according to the present invention may be in various forms such as powders obtained by mixing each of the ingredients, granules formed by optionally adding water to the mixture of the ingredients, a lump, tablets obtained by pressing the mixture of the ingredients, and the like.

The insecticidally active ingredient may be added and mixed in the poison bait either as it is, or in the form of formulations such as powders, wettable powders, microcapsules, emulsion, oil, and the like.

The poison bait for controlling pest insects according to the present invention is the most suitable for controlling cockroaches such as American cockroach (*Periplaneta americana* LINNE), German cockroach (*Blattella germanica* LINNE), smoky brown cockroach (*Periplaneta fuliginosa* SELVILLE) and the like, and also usable for controlling other pest insects, for example, ants such as *Monomorium pharaonis* LINNE, *Formica japonica* MOTSCHULSKY, and the like, Death watch beetles such as *Lasioderma serricorne* FABRICIUS, *Stegobium paniceum* LINNE and the like, Darkling beetles such as *Tribolium castaneum* HERBST, *Tribolium confusum* JACQUELIN DU VAL, Flat bark beetles such as *Oryzaephilus surinamensis* LINNE, *Cryptolestes pusillus* SCHOENHERR and the like and termites such as *Coptotermes formosanus* SHIRAKI, *Reticulitermes speratus* KOLBE and the like.

The poison bait for controlling pest insects according to the present invention can be used in order to control the pest insects by placing said bait in a locus in which the pest insects live or through which they pass.

EXAMPLES

The present invention will now be explained with reference to the following Preparation Examples and Test Examples, which should not be construed as a limitation upon the scope of the invention.

In the Examples, "WORCESTER SAUCE" made by Kagome Co., Ltd. was used as the Worcester sauce, and "SAUCE SPICE FLAVOR No.B-82404" made by Takasago International Corporation was used as the sauce spice flavor, unless described otherwise.

Preparation Example 1

A poison bait was obtained by sufficiently mixing 0.5 part by weight of Fenitrothion [O,O-dimethyl O-(3-methyl-4-nitrophenyl) phosphorothioate], 15 parts by weight of Worcester sauce, 20 parts by weight of sesame oil, 10 parts by weight of wheat flour, 4.5 parts by weight of dextrin and 50 parts by weight of raw sugar.

Preparation Example 2

A poison bait was obtained by sufficiently mixing 0.5 part by weight of Fenitrothion, 10 parts by weight of Worcester sauce, 20 parts by weight of sesame oil, 20 parts by weight of wheat flour, 19.5 parts by weight of dextrin and 30 parts by weight of raw sugar.

Preparation Example 3

A poison bait was obtained by sufficiently mixing 0.5 part by weight of Fenitrothion, 2 parts by weight of Worcester sauce, 10 parts by weight of soybean oil, 10 parts by weight of rape seed oil, 50 parts by weight of wheat flour, 7.5 parts by weight of dextrin and 20 parts by weight of granulated sugar.

Preparation Example 4

A poison bait was obtained by sufficiently mixing 0.5 part by weight of Fenitrothion, 15 parts by weight of Worcester sauce, 10 parts by weight of soybean oil, 10 parts by weight of rape seed oil, 10 parts by weight of wheat flour, 24.5 parts by weight of dextrin and 30 parts by weight of granulated sugar.

Preparation Example 5

A poison bait was obtained by sufficiently mixing 0.5 part by weight of Fenitrothion, 10 parts by weight of Worcester sauce, 20 parts by weight of sesame oil, 10 parts by weight of soybean oil, 20 parts by weight of wheat flour, 19.5 parts by weight of dextrin, 10 parts by weight of raw sugar and 10 parts by weight of granulated sugar.

Preparation Example 6

A poison bait was obtained by sufficiently mixing 0.5 part by weight of Fenitrothion, 2 parts by weight of Worcester sauce, 10 parts by weight of sesame oil, 20 parts by weight of soybean oil, 50 parts by weight of wheat flour, 7.5 parts by weight of dextrin and 10 parts by weight of raw sugar.

Preparation Example 7

A poison bait was obtained by sufficiently mixing 0.5 part by weight of Fenitrothion, 15 parts by weight of powdered Worcester sauce, 20 parts by weight of sesame oil, 10 parts by weight of wheat flour, 4.5 parts by weight of dextrin and 50 parts by weight of raw sugar.

Preparation Example 8

A poison bait was obtained by sufficiently mixing 0.5 part by weight of Fenitrothion, 10 parts by weight of powdered Worcester sauce, 20 parts by weight of sesame oil, 20 parts by weight of wheat flour, 19.5 parts by weight of dextrin and 30 parts by weight of raw sugar.

Preparation Example 9

A poison bait was obtained by sufficiently mixing 0.5 part by weight of Fenitrothion, 2 parts by weight of powdered Worcester sauce, 10 parts by weight of soybean oil, 10 parts by weight of rape seed oil, 50 parts by weight of wheat flour, 7.5 parts by weight of dextrin and 20 parts by weight of granulated sugar.

Preparation Example 10

A poison bait was obtained by sufficiently mixing 0.5 part by weight of Fenitrothion, 15 parts by weight of powdered Worcester sauce, 10 parts by weight of soybean oil, 10 parts by weight of rape seed oil, 10 parts by weight of wheat flour, 24.5 parts by weight of dextrin and 30 parts by weight of granulated sugar.

Preparation Example 11

A poison bait was obtained by sufficiently mixing 0.5 part by weight of Fenitrothion, 10 parts by weight of powdered Worcester sauce, 20 parts by weight of sesame oil, 10 parts by weight of soybean oil, 20 parts by weight of wheat flour, 19.5 parts by weight of dextrin and 10 parts by weight of raw sugar and 10 parts by weight of granulated sugar.

Preparation Example 12

A poison bait was obtained by sufficiently mixing 0.5 part by weight of Fenitrothion, 2 parts by weight of powdered Worcester sauce, 10 parts by weight of sesame oil, 20 parts by weight of soybean oil, 50 parts by weight of wheat flour, 7.5 parts by weight of dextrin and 10 parts by weight of raw sugar.

Preparation Example 13

A poison bait was obtained by sufficiently mixing 0.5 part by weight of Fenitrothion, 2 parts by weight of sauce spice flavor, 20 parts by weight of sesame oil, 10 parts by weight of wheat flour, 17.5 parts by weight of dextrin and 50 parts by weight of raw sugar.

Preparation Example 14

A poison bait was obtained by sufficiently mixing 0.5 part by weight of Fenitrothion, 2 parts by weight of sauce spice flavor, 20 parts by weight of sesame oil, 20 parts by weight of wheat flour, 27.5 parts by weight of dextrin and 30 parts by weight of raw sugar.

Preparation Example 15

A poison bait was obtained by sufficiently mixing 0.5 part by weight of Fenitrothion, 2 parts by weight of sauce spice flavor, 10 parts by weight of soybean oil, 10 parts by weight of rape seed oil, 40 parts by weight of wheat flour, 7.5 parts by weight of dextrin and 30 parts by weight of raw sugar.

Preparation Example 16

A poison bait was obtained by sufficiently mixing 0.5 part by weight of Fenitrothion, 2 parts by weight of sauce spice flavor, 10 parts by weight of soybean oil, 10 parts by weight of rape seed oil, 10 parts by weight of wheat flour, 37.5 parts by weight of dextrin and 30 parts by weight of granulated sugar.

Preparation Example 17

A poison bait was obtained by sufficiently mixing 0.5 part by weight of Fenitrothion, 2 parts by weight of sauce spice flavor, 20 parts by weight of sesame oil, 10 parts by weight of soybean oil, 20 parts by weight of wheat flour, 27.5 parts by weight of dextrin, 10 parts by weight of raw sugar and 10 parts by weight of granulated sugar.

Preparation Example 18

A poison bait was obtained by sufficiently mixing 0.5 part by weight of Fenitrothion, 2 parts by weight of sauce spice flavor, 10 parts by weight of sesame oil, 20 parts by weight of soybean oil, 50 parts by weight of wheat flour, 7.5 parts by weight of dextrin and 10 parts by weight of raw sugar.

Preparation Example 19

A poison bait was obtained by sufficiently mixing 0.5 part by weight of Fenitrothion, 0.01 part by weight of sauce spice flavor, 20 parts by weight of sesame oil, 10 parts by weight of wheat flour, 19.49 parts by weight of dextrin and 50 parts by weight of raw sugar.

Preparation Example 20

A poison bait was obtained by sufficiently mixing 0.5 part by weight of Fenitrothion, 0.01 part by weight of sauce spice flavor, 20 parts by weight of sesame oil, 20 parts by weight of wheat flour, 29.49 parts by weight of dextrin and 30 parts by weight of raw sugar.

Preparation Example 21

A poison bait was obtained by sufficiently mixing 0.5 part by weight of Fenitrothion, 0.01 part by weight of sauce spice flavor, 10 parts by weight of soybean oil, 10 parts by weight of rape seed oil, 50 parts by weight of wheat flour, 9.49 parts by weight of dextrin and 20 parts by weight of granulated sugar.

Preparation Example 22

A poison bait was obtained by sufficiently mixing 0.5 part by weight of Fenitrothion, 0.01 part by weight of sauce spice flavor, 10 parts by weight of soybean oil, 10 parts by weight of rape seed oil, 10 parts by weight of wheat flour, 39.49 parts by weight of dextrin and 30 parts by weight of granulated sugar.

Preparation Example 23

A poison bait was obtained by sufficiently mixing 0.5 part by weight of Fenitrothion, 0.01 part by weight of sauce spice flavor, 20 parts by weight of sesame oil, 10 parts by weight of soybean oil, 20 parts by weight of wheat flour, 29.49 parts by weight of dextrin, 10 parts by weight of raw sugar and 10 parts by weight of granulated sugar.

Preparation Example 24

A poison bait was obtained by sufficiently mixing 0.5 part by weight of Fenitrothion, 0.01 part by weight of sauce spice flavor, 10 parts by weight of sesame oil, 20 parts by weight of soybean oil, 50 parts by weight of wheat flour, 9.49 parts by weight of dextrin and 10 parts by weight of raw sugar.

Some Examples of preparation of the poison bait used for comparison in Test Example described later are shown below as Reference Examples.

Reference Example 1

A poison bait was obtained by the same manner described in Preparation Example 4 except that, further 10 parts by weight of wheat flour and further 5 parts by weight of dextrin were used instead of 15 parts by weight of Worcester sauce.

Reference Example 2

A poison bait was obtained by sufficiently mixing 0.5 part by weight of Fenitrothion, 20 parts by weight of sesame oil, 20 parts by weight of wheat flour, 29.5 parts by weight of dextrin, 10 parts by weight of powdered krill and 20 parts by weight of granulated sugar.

Reference Example 3

A poison bait was obtained by sufficiently mixing 0.5 part by weight of Fenitrothion, 10 parts by weight of Worcester sauce, 10 parts by weight of powdered silk moth pupa, 30 parts by weight of wheat flour, 19.5 parts by weight of dextrin and 30 parts by weight of raw sugar.

Text Example

Each 5 of male and female adult German cockroaches were put in a container having a base area of 0.24 m². About 5 g of the poison bait and 25 g of the ordinary food for rearing cockroaches were placed in the container. After a week, mortality(%) was calculated.

Two strains of the German cockroaches were used for experiments. All the poison baits according to the present invention prepared in Preparation Examples 1–24 showed a mortality of 80% or above.

On the other hand, the poison bait for comparison prepared in Reference Examples 1 and 2 showed mortality of 80% or above against only 1 strain of the cockroaches but a mortality of less than 80% against the other strain. Also, the poison bait obtained in Reference Example 3 showed a mortality of less than 80% against the both strains.

While German cockroaches may show different feeding preference depending on strain and rearing conditions, it was proved that the poison bait according to the present invention showed excellent feeding preference and, as the result, good effect for controlling cockroaches. Particularly, the poison bait according to the present invention containing both of the sauce for seasoning and the vegetable oil showed superior controlling effect to the poison bait obtained in Reference Examples 1 and 2 which do not contain the sauce for seasoning and the poison bait obtained in Reference Example 3 which contain the sauce for seasoning but does not the vegetable oil.

It can be concluded from the above test that the poison bait according to the present invention shows good controlling effect against cockroaches and the like on the basis of its excellent feeding preference.

What is claimed is:

1. A poison bait for controlling pest insects, which comprises (a) an insecticidally active ingredient, (b) a sauce for seasoning and (c) a vegetable oil.

2. A poison bait for controlling pest insects according to claim 1, which comprises 0.05–10% by weight of an insecticidally active ingredient, 1–20% by weight of a sauce for seasoning and 10–50% by weight of a vegetable oil.

3. A poison bait for controlling pest insects according to claim 1, which further comprises at least one kind selected from the group consisting of grain powder, dextrin and sugar.

4. A poison bait for controlling pest insects according to claim 3 which comprises 0.05–10% by weight of an insecticidally active ingredient, 1–20% by weight of a sauce for seasoning, 10–50% by weight of a vegetable oil and 40–85% by weight of at least one kind selected from the group consisting of grain powder, dextrin and sugar.

5. A poison bait for controlling pest insects according to claim 1, 2, 3 or 4, wherein the pest insects are cockroaches.

6. A method for controlling pest insects which comprises placing the poison bait for controlling pest insects according to claim 1 in a locus in which the pest insects live or through which the pest insects pass.

7. A method according to claim 6, wherein the pest insects are cockroaches.

8. A poison bait for controlling pest insects according to claim 1, wherein the sauce for seasoning is Worcester sauce, medium thick sauce or thick sauce.

9. A poison bait for controlling pest insects according to claim 1, wherein the sauce for seasoning is Worcester sauce.

10. A poison bait for controlling pest insects according to claim 2, wherein the sauce for seasoning is Worcester sauce, medium thick sauce or thick sauce.

11. A poison bait for controlling pest insects according to claim 2, wherein the sauce for seasoning is Worcester sauce.

12. A poison bait for controlling pest insects according to claim 3, wherein the sauce for seasoning is Worcester sauce, medium thick sauce or thick sauce.

13. A poison bait for controlling pest insects according to claim 3, wherein the sauce for seasoning is Worcester sauce.

14. A poison bait for controlling pest insects according to claim 4, wherein the sauce for seasoning is Worcester sauce, medium thick sauce or thick sauce.

15. A poison bait for controlling pest insects according to claim 4, wherein the sauce for seasoning is Worcester sauce.

* * * * *